United States Patent [19]

Jackisch

[11] 4,338,474

[45] Jul. 6, 1982

[54] STABILIZATION OF DIBROMOSTYRENE

[75] Inventor: Philip F. Jackisch, Royal Oak, Mich.

[73] Assignee: Ethyl Corporation, Richmond, Va.

[21] Appl. No.: 130,186

[22] Filed: Mar. 13, 1980

[51] Int. Cl.$^3$ .................. C07C 17/42; C09K 15/26
[52] U.S. Cl. ............................. 570/105; 252/1; 252/402; 570/106
[58] Field of Search ............ 252/1, 402; 570/105, 570/106

[56] References Cited

U.S. PATENT DOCUMENTS

| | | | |
|---|---|---|---|
| 2,181,102 | 11/1939 | Stoesser et al. | 570/105 X |
| 2,965,565 | 12/1960 | McDonald | 252/1 |
| 3,225,108 | 12/1965 | Sturgis | 570/105 |
| 3,898,294 | 8/1975 | Cooley | 570/103 X |
| 4,276,189 | 6/1981 | Jackisch | 252/404 |

FOREIGN PATENT DOCUMENTS 1230979  5/1971  United Kingdom ............... 570/105

OTHER PUBLICATIONS

Ravve: "Organic Chemistry of Macromolecules", Marcel Dekker, Inc., New York (1967), pp. 7–72.
"Textbook of Polymer Science", 2nd Ed., John Wiley and Sons, Inc., New York, (1971), p. 400.
"Reactivity, Mechanism and Structure in Polymer Chemistry", John Wiley and Sons, New York, (1974), p. 216.

*Primary Examiner*—Richard D. Lovering
*Attorney, Agent, or Firm*—Donald L. Johnson; Joseph D. Odenweller; John F. Hunt

[57] ABSTRACT

Dibromostyrene is stabilized against unwanted polymerization by incorporating therein a stabilizing amount of phenothiazine or a substituted phenothiazine such as 3,3'-dioctylphenothiazine. The phenolthiazine can be admixed with a dihydroxy aromatic compound such as 4-methyl catechol.

10 Claims, 1 Drawing Figure

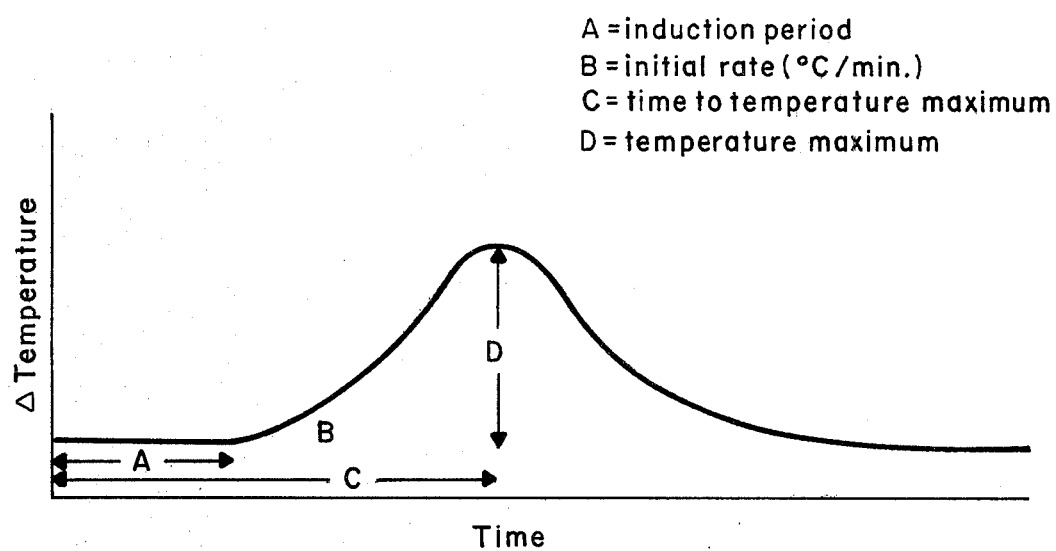
Representative Differential Thermal
Analysis Curve of Polymerization

STABILIZATION OF DIBROMOSTYRENE

BACKGROUND OF THE INVENTION

Dibromostyrene, which has been suggested as a flame retardant monomer, has a considerable tendency to undergo polymerization during storage. This polymerization tendency is greater than with styrene itself. It has been suggested in British Pat. No. 1,230,979, that dibromostyrene be stabilized with picric acid or a mixture of picric acid and (i) a quinone such as hydroquinone or benzoquinone or (ii) a phenol such as tert-butyl catechol.

SUMMARY OF THE INVENTION

This invention comprises the discovery that undesired polymerization of dibromostyrene during storage is reduced if the dibromostyrene is intimately mixed with a phenothiazine having the formula

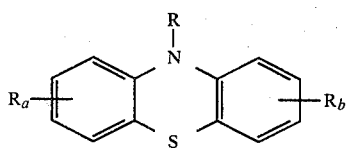

wherein each R is alike or different and is selected from the class consisting of hydrogen and lower alkyl groups of up to about 10 carbon atoms and a and b are independently equal to zero or a positive whole number of from 1 to 2.

Two preferred compounds of the above formula are phenothiazine and 3,3'-dioctylphenothiazine. Such phenothiazines can be admixed with phenols having the formula

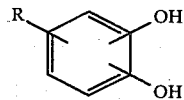

wherein R is an alkyl radical to obtain stabilizer compositions of this invention that can be used to delay the onset of undesired polymerization of dibromostyrene.

DESCRIPTION OF THE DRAWING

The drawing shows a representation of a differential thermal analysis (DTA) curve obtained when the polymerization of dibromostyrene with an inhibitor is followed by DTA using the apparatus and procedure described herein. As shown, the value for (A) indicates how long the induction period before the polymerization ensues, while the value for (C) indicates the time for the polymerization to reach its maximum. The slope of the curve at (B) after the terminus of (A) is an indication of the polymerization rate, while the height of (C) gives the temperature maximum reached.

Without a polymerization inhibitor, the period indicated by (A) is non-existent or very short. With a polymerization retardant, it makes the slope of the line at (B) less steep and diminishes the height of (D). The average polymerization rate in °C. per unit time can be calculated from the slope of the line connecting the end of (A) with the maximum of the curve; i.e. where the curve is intercepted by the height (D).

DESCRIPTION OF PREFERRED EMBODIMENTS

This invention works well when applied to dibromostyrene made by dehydrohalogenation such as dehydrobromination of a 2-bromoethyldibromobenzene. A preferred method for the dehydrobromination is that described in my copending application entitled "Preparation of Dibromostyrene". The invention also gives better results when the dibromostyrene contains less than about 0.1 weight percent of β-bromoethyldibromobenzene impurity and less than about 2 weight percent of tribromostyrene impurity. However, the tribromostyrene level may be 8-9 percent or higher. Dibromostyrene preparations usually are largely 2,4-dibromostyrene or 2,3-dibromostyrene.

The object of the invention is to stabilize the unwanted polymerization of dibromostyrene which can occur upon storage. Thus, the process of this invention is the stabilization of dibromostyrene at ordinary storage temperatures, usually no more than about 35°-38° C. For testing, the temperature to which the dibromostyrene and stabilizer system are exposed can be much higher to accelerate obtaining the test results.

The stabilizers of this invention have the nucleus

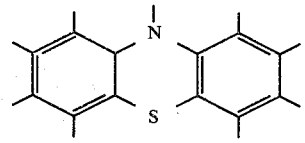

wherein the unsatisfied valences are bonded to radicals which do not unduly hinder the ability of the stabilization activity to take place. A skilled practitioner using the test procedure described in the Example can readily determine if a compound having the above depicted nucleus is an additive of this invention. If use of the test described in the example shows that the compound under investigation gives a longer induction period than that determined for the untreated dibromostyrene, then the compound under investigation is an additive or stabilizer of this invention.

The unsatisfied valences, in the formula of the active nucleus depicted above, can be bonded to hydrogen or typically, a hydrocarbyl group. Preferably, the hydrocarbyl group is rather small and not of such complexity as to either make the compound economically unattractive or unduly low in reactivity on a weight of additive basis. Further, as shown in the example below, good activity can be obtained with a compound of simple structure. Hence, unless there is a gain in cost-effectiveness or other useful property or characteristic, then there may not be an advantage in substituting a more heavily substituted phenylene diamine for the lower alkyl substituted products wherein each radical bonded to nitrogen (and not the phenylene nucleus) is hydrogen or an alkyl group of one to five, more preferably one or two carbons.

The stabilizers of this invention are preferably used in a concentration of from about 20 to about 2000 ppm, more preferably from about 100 to about 600 ppm.

The phenothiazine additives discussed above can be admixed with a stabilizer enhancing amount of a dihydroxyphenol

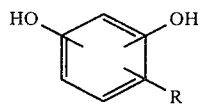

wherein R is a lower alkyl group, preferably a group of up to about 2 carbon atoms. Compositions comprising a mixture of a dihydroxyphenol and a phenothiazine described above are an embodiment of this invention, and such mixtures can be added to dibromostyrene to delay the onset of undesirable polymerization.

With regard to the dihydroxydiphenyls of this invention, their identity can be determined by testing as discussed above for the thiazine compounds. As with the thiazines, the dihydroxy compounds are preferably lightly substituted except, when more extensive substitution confers a desirable utility on the mixture, the phenol is blended with it. A preferred dihydroxy compound is 4-methylcatechol. The dihydroxy phenols are used in an amount of from about 20 to about 2000 ppm.

EXAMPLE 1

A differential thermal analysis apparatus was constructed to measure the heat of polymerization of stored monomer samples. Two thermopiles were constructed (originally with 6 thermocouples each but recently with 5) with iron-Constantin junctions. Sample containers consisted of 18 ml widemouthed bottles with caps drilled with a hole through which was fitted a piece of glass tubing sealed at the bottom end to form a thermowell. The glass tubes were 8 mm in outside diameter and 90 mm long and were filled with 5 drops of Dow Corning No. 200 Silicone Oil to help in heat transfer. The thermopiles were inserted into the thermowells of two cells, one containing an inert fluid (originally m-dibromobenzene but more recently Dow Corning No. 200 Silicone Oil), and the other approximately 15 g (9 ml) of dibromostyrene or an equal volume of bromostyrene or styrene. The sample and reference cells were placed in a wooden holder in a Blue M, Stabil-Therm Poweromatic 70 oven. The oven temperature was measured with a Doric Trendicator 400A type K °C. digital pyrometer connected to a thermocouple with its end in the wooden cell holder. The temperature differential between the reference cell and the monomer-containing cell was recorded on a Houston Instruments OmniScribe recorder at either 1 millivolt or 10 millivolts full scale (equal to 4.8 or 48 degrees C).

The dibromostyrene used in the test contained 1.1 weight percent monobromostyrene and 8.7 percent tribromostyrene.

Results of testing were as follows:

| Inhibitor* | Induction Period | Initial Poly. Rate | Average Poly. Rate | Time of Max. Rate | Temp. Max. |
|---|---|---|---|---|---|
| None | 0 | 3.8° hr | 4.4° hr | 1.5 hr | 6.3° C. |
| Phenothiazine | 12.4 | 0.046 | 0.14 | 22.1 | 1.3 |
| 3,3'-Dicyclo-phenothiazine | 5.8 | 67 | 1.4 | 8.1 | 3.2 |
| Phenothiazine and 4-methyl-catechol | 24.3 | 0.035 | 0.029 | 34.2 | 0.3 |
| Phenothiazine and 4-tert-butyl catechol | 0 | 0.18 | 0.030 | 37.8 | 1.1 |
| N,N,N',N'-tetra-methyl-p-phenylene diamine and phenol-thiazine | 19.7 | 0.020 | 0.058 | 43.9 | 1.4 |

*400 ppm of each

The above results suggest similar results can be obtained when phenothiazines as described above are used in amounts of about 20 to 2000 ppm alone or admixed with a dihydroxyphenol as described above used in the amounts of from about 20 to 2000 ppm. Likewise, the above results suggest that the phenothiazines can be combined with a phenylene-p-diamine wherein each nitrogen atom is substituted by hydrogen or a lower alkyl radical of up to about 5 carbon atoms used in an amount of from about 20 to about 2000 ppm.

I claim:

1. As a composition of matter, dibromostyrene containing a stabilizer amount of a compound having the formula

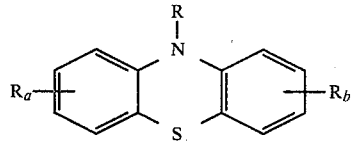

wherein each R is alike or different and is selected from the class consisting of hydrogen and lower alkyl groups of up to about 10 carbon atoms and a and b are independently equal to zero or a positive whole number of from 1 to 2.

2. A composition of claim 1 wherein the amount of said stabilizer is from about 20 to about 2000 ppm.

3. A composition of claim 2 wherein said compound is phenothiazine.

4. A composition of claim 1 wherein said stabilizer is admixed with a stabilizer enhancing amount of a dihydroxyphenol

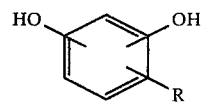

wherein R is a lower alkyl group of up to about 4 carbon atoms.

5. A composition of claim 4 wherein said stabilizer enhancing amount is from about 20 to about 2000 ppm.

6. A composition of claim 4 wherein said dihydroxyphenol is 4-methyl catechol.

7. A composition of claim 6 wherein the amount of said 4-methyl catechol is from about 20 to about 2000 ppm.

8. A composition of claim 4 wherein said dihydroxyphenol is 4-tert-butyl catechol.

9. A composition of claim 8 wherein the amount of said 4-tert-butyl catechol is from about 20 to about 2000 ppm.

10. As a composition of matter, a mixture of dibromostyrene, a phenothiazine compound having the formula

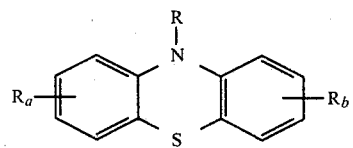

wherein each R is alike or different and is selected from the class consisting of hydrogen and lower alkyl groups of up to about 10 carbon atoms and a and b are independently equal to zero or a positive whole number of from 1 to 2; and a phenolic compound of the formula

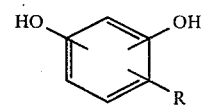

wherein R is a lower alkyl group of about 4 carbon atoms wherein the weight ratio of said phenothiazine to said phenol is from about 0.1 to 10 to 1.

* * * * *